(12) United States Patent
Tait

(10) Patent No.: US 11,763,792 B2
(45) Date of Patent: Sep. 19, 2023

(54) NOISE CANCELLATION

(71) Applicant: Cirrus Logic International Semiconductor Ltd., Edinburgh (GB)

(72) Inventor: Calum J. Tait, Penicuik (GB)

(73) Assignee: Cirrus Logic Inc., Austin, TX (US)

(*) Notice: Subject to any disclaimer, the term of this patent is extended or adjusted under 35 U.S.C. 154(b) by 0 days.

(21) Appl. No.: 17/465,288

(22) Filed: Sep. 2, 2021

(65) Prior Publication Data
US 2022/0130366 A1 Apr. 28, 2022

Related U.S. Application Data

(60) Provisional application No. 63/105,633, filed on Oct. 26, 2020.

(30) Foreign Application Priority Data

Nov. 24, 2020 (GB) .................... 2018491

(51) Int. Cl.
*G10K 11/178* (2006.01)

(52) U.S. Cl.
CPC .. *G10K 11/17854* (2018.01); *G10K 11/17823* (2018.01); *G10K 11/17881* (2018.01); *G10K 2210/1081* (2013.01); *G10K 2210/3026* (2013.01); *G10K 2210/3027* (2013.01); *G10K 2210/3028* (2013.01); *G10K 2210/3044* (2013.01); *G10K 2210/3056* (2013.01)

(58) Field of Classification Search
CPC ... G10K 2210/1081; G10K 2210/3026; G10K 2210/3027; G10K 11/178; G10K 11/17821; G10K 11/17881; G10K 11/17883; G10K 11/17879

See application file for complete search history.

(56) References Cited

U.S. PATENT DOCUMENTS

2012/0140917 A1* 6/2012 Nicholson ........ G10K 11/17881
379/392.01
2021/0258676 A1* 8/2021 Liang .................. H04R 1/1016

FOREIGN PATENT DOCUMENTS

EP 3869819 A2 8/2021

OTHER PUBLICATIONS

Examination Report under Section 17, UKIPO, Application No. GB2018491.7, dated May 19, 2022.

* cited by examiner

*Primary Examiner* — Kile O Blair
(74) *Attorney, Agent, or Firm* — Jackson Walker L.L.P

(57) ABSTRACT

Circuitry for noise cancellation in a headset worn by a user, the circuitry comprising: an input for receiving one or more heartbeat signals representative of a heartbeat of the user; a processor for generating a heartbeat noise cancellation signal based on the one or more heartbeat signal, the heartbeat noise cancellation signal to cancel a noise associated with the heartbeat in the user's ear; an output for outputting the heartbeat noise cancellation signal to a transducer of the headset.

29 Claims, 6 Drawing Sheets

NOISE CANCELLATION

The present disclosure claims priority to U.S. Provisional Patent Application Ser. No. 63/105,633, filed Oct. 26, 2020, and United Kingdom Patent Application No. 2018491.7, filed Nov. 24, 2020, each of which is incorporated by reference herein in its entirety.

TECHNICAL FIELD

The present disclosure relates to noise cancellation in headsets and in particular cancellation of noise due to a heartbeat.

BACKGROUND

Headsets are used to deliver sound to one or both ears of a user, such as music or audio files or telephony signals. Modern headsets typically also capture sound from the surrounding environment, such as the user's voice for voice recording or telephony, or background noise signals to be used to enhance signal processing by the device and user experience.

When a user wears such headsets, particularly during exercise, the flow of blood through blood vessels close to the user's eardrum and ear canal, as well as blood flow further afield, can cause an artefact audible to the user which is exacerbated by the headset partially or fully occluding the user's ear canal.

SUMMARY

Embodiments of the present disclosure aim to address or at least ameliorate one or more of the above issues through the generation of audio signals for cancelling the artefact audible to the user due to the user's heartbeat. By monitoring the user's heartbeat through the use of one or more sensors, such as a microphone, an inertial measurement unit (IMU) and/or a heart or pulse rate sensor, for example, embodiments of the present disclosure aim to generate and apply a heartbeat noise cancellation signal (i.e. an "anti-noise" or "anti-heartbeat" signal) to a transducer located proximate the user's ear canal to remove or at least ameliorate the heartbeat artefact from the user's hearing.

According to an aspect of the disclosure, there is provided circuitry for noise cancellation in a headset worn by a user, the circuitry comprising: an input for receiving one or more heartbeat signals representative of a heartbeat of the user; a processor for generating a heartbeat noise cancellation signal based on the one or more heartbeat signal, the heartbeat noise cancellation signal to cancel a noise associated with the heartbeat in the user's ear; an output for outputting the heartbeat noise cancellation signal to a transducer of the headset.

The one or more heartbeat signals may comprise one or more of: a) an audio signal from an internal microphone of the headset; b) an IMU signal from an inertial measurement unit, IMU of the headset; c) a heartbeat signal from a heartbeat sensor. The heartbeat sensor may be a photoplethysmography, PPG, sensor or an electrocardiography, ECG, sensor.

The processor may be configured to: filter the audio signal or the IMU signal; and output the filtered audio signal or the filtered IMU signal as the heartbeat noise cancellation signal.

Filtering of the audio signal or the IMU signal may comprise applying a low pass filter to remove noise. Filtering of the audio signal or the IMU signal may comprise: adjusting a gain of one or more frequency components of the audio signal or the IMU signal at frequencies of the noise associated with the heartbeat in the user's ear.

The processor may be configured to monitor timing of the heartbeat based on the one or more heartbeat signals and filter the audio signal or the IMU signal based on the timing. The timing of the heartbeat may comprises a heartrate. The timing of the heartbeat may comprise a heart rhythm. The heart rhythm may comprise one or more of: a) timing of a contraction or dilation of one or more muscles of the heart; and b) timing of an opening or closing of one or more valves of the heart.

The processor may be configured to filter the audio signal with a first filter characteristic during a first time period and a second filter characteristic during a second time period. The first time period may be an S1 period of a cardiac cycle and the second time period may be an S2 period of a cardiac cycle. In some embodiments, the processor may be configured to switch between a first filter for applying the first filter characteristic and a second filter for applying the second filter characteristic to the audio signal. In some embodiments, the processor may be configured to change a one or more filter co-efficients of a common filter to switch between filtering the audio signal with the first filter characteristic and filtering the audio signal with the second filtering characteristic.

The one or more characteristics of the filtering may be dependent on an amplitude of one or more features in one or more of the one or more heartbeat signals.

The processor may be configured to: monitor a sound level at the headset; and generate the heartbeat noise cancellation signal when the sound level is below a predetermined threshold level at which the noise associated with the heartbeat is audible to the user.

The sound level may be monitored using one or more of the IMU signal, or the audio signal from the internal microphone, or an audio signal from an external microphone of the headset.

The processor may be configured to: generate the heartbeat noise cancellation signal when a heartrate of the heartbeat exceeds a predetermined heartbeat threshold at which the noise associated with the heartbeat is audible to the user.

The processor may be further configured to generate a feedback noise cancellation signal based on the audio signal received from the internal microphone. The output may be configured to output the feedback noise cancellation signal to the transducer.

The circuitry may further comprise a second input for receiving an external audio signal from an external microphone; wherein the processor is further configured to generate a feedforward noise cancellation signal based on the external audio signal from the external microphone; wherein the output is configured to output the feedforward noise cancellation signal to the transducer.

According to another aspect of the disclosure, there is provided a headphone comprising the circuitry described above. The headphone may be configured to partially or fully occlude the ear of the user.

According to another aspect of the disclosure, there is provided an electronic device comprising circuitry as described above. The electronic device may be at least one of: a portable device; a battery powered device; a communications device; a computing device; a mobile telephone; a laptop, notebook or tablet computer; a personal media player; a gaming device; and a wearable device.

According to another aspect of the disclosure, there is provided a headphone, comprising an internal microphone; an external microphone; a transducer; and one or more processors configured to: receive one or more heartbeat signals representative of a heartbeat of a user; generate a heartbeat noise cancellation signal based on the one or more heartbeat signal, the heartbeat noise cancellation signal to cancel a noise associated with the heartbeat in the user's ear; and output the heartbeat noise cancellation signal to the transducer.

According to another aspect of the disclosure, there is provided circuitry configured to: obtain a heartbeat signal for a user; apply an anti-noise signal to the ear of the user to cancel a sound of the user's heartbeat in the user's ear, based on the heartbeat signal.

According to another aspect of the disclosure, there is provided a headphone, comprising: a speaker; and a signal processor configured to: receive one or more signals representative of a heartbeat of a user; generate a heartbeat noise cancellation signal based on the one or more representative signals and output the heartbeat noise cancellation signal to the speaker.

According to another aspect of the disclosure, there is provided circuitry configured to: receive a heartbeat signal; generate an anti-heartbeat for application to a speaker.

According to another aspect of the disclosure, there is provided circuitry configured to: receive a signal representative of the function of a human heart; generate an antiphase signal representative of the function of a human heart for application to a speaker.

According to another aspect of the disclosure, there is provided a method of noise cancellation in a headset worn by a user, comprising: obtaining one or more heartbeat signal representative of a heartbeat of the user; generating a heartbeat noise cancellation signal based on the heartbeat signal, the heartbeat noise cancellation signal to cancel a noise associated with the heartbeat in the user's ear; applying the noise cancellation signal to a transducer of the headset.

According to another aspect of the disclosure, there is provided a non-transitory machine readable storage medium having instruction stored thereon which, when executed by a processor cause the processor to: obtain one or more heartbeat signal representative of a heartbeat of the user; generate a heartbeat noise cancellation signal based on the heartbeat signal, the heartbeat noise cancellation signal to cancel a noise associated with the heartbeat in the user's ear; apply the noise cancellation signal to a transducer of the headset.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the present disclosure relate to a realisation by the inventors that the heartbeat of a user wearing headsets such as those described below, particularly after strenuous activity, is audible to the user. This phenomenon is exacerbated by partial or full occlusion of the ear canal with the headphone which, due to the "occlusion effect" causes amplification of low frequency sound (i.e. low frequency boom) in the ear canal. Low-frequency sound associated with heartbeat, due to the pulsing of blood through the carotid artery which is positioned very close to the eardrum of the user, is thus particularly loud to users of ear occluding headsets. Bone and/or tissue noise conduction of a user's heartbeat can also contribute to the heartbeat of a user being audible to that user.

Figure 1:
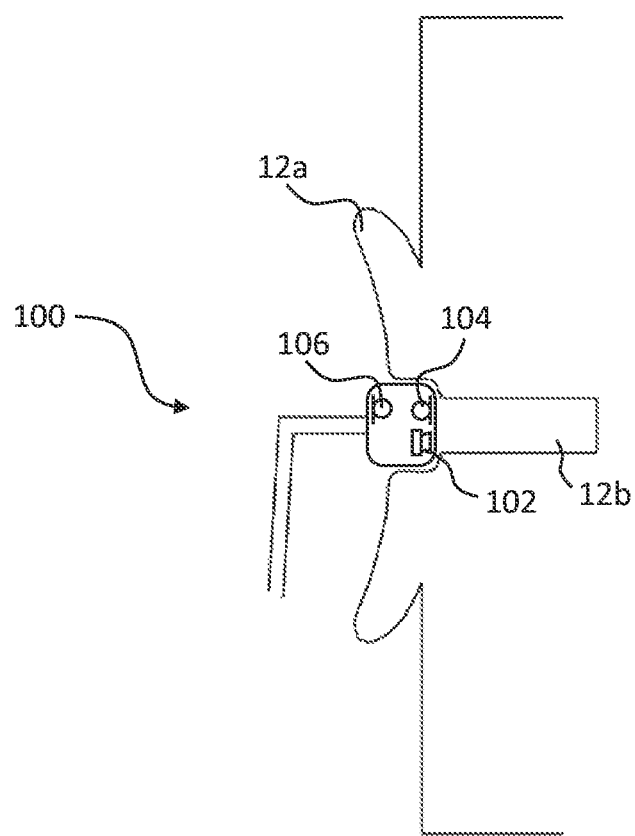
FIG. 1 is a diagram of a headphone located in ear of a user.

FIG. 1 shows a schematic diagram of a user's ear, comprising the (external) pinna or auricle 12a, and the (internal) ear canal 12b. A personal audio device comprising an intra-concha headphone 100 (or earphone) sits inside the user's concha cavity. The intra-concha headphone may fit loosely within the cavity, allowing the flow of air into and out of the user's ear canal 12b which results in partial occlusion of the ear canal of the user. Alternatively, the headphone 100 may form a tight seal with the ear canal which may result in full occlusion.

The headphone 100 comprises one or more loudspeakers 102 positioned on an internal surface of the headphone 100 and arranged to generate acoustic signals towards the user's ear and particularly the ear canal 12b. The earphone further comprises one or more microphones 104, known as error microphone(s) or internal microphone(s), positioned on an internal surface of the earphone, arranged to detect acoustic signals within the internal volume defined by the headphone 100 and the ear canal 12b. The headphone 100 may also comprise one or more microphones 106, known as reference microphone(s) or external microphone(s), positioned on an external surface of the headphone 100 and configured to detect environmental noise incident at the user's ear.

The headphone 100 may be able to perform active noise cancellation, to reduce the amount of noise experienced by the user of the headphone 100. Active noise cancellation typically operates by detecting the noise (i.e. with a microphone) and generating a signal (i.e. with the loudspeaker) that has the same amplitude as the noise signal but is opposite in phase. The generated signal thus interferes destructively with the noise and so cancels or at least lessens the noise experienced by the user. Active noise cancellation may operate on the basis of feedback signals, feedforward signals, or a combination of both, i.e. a hybrid noise cancellation arrangement. Feedforward active noise cancellation utilizes the one or more microphones 106 on an external surface of the headphone 100, operative to detect the environmental noise before it reaches the user's ear. The detected noise is processed, and the cancellation signal generated so as to inversely match the incoming noise as it arrives at the user's ear thus cancelling, or at least reducing, the noise. Feedback active noise cancellation utilizes the one or more error microphones 104, also known as feedback microphones, positioned on the internal surface of the headphone 100, operative to detect the combination of the noise and the audio playback signal generated by the one or more loudspeakers 102. This combination is used in a feedback loop, together with knowledge of the audio playback signal, to adjust the cancelling signal generated by the loudspeaker 102 and so reduce or cancel the noise. The microphones 104, 106 shown in FIG. 1 may therefore form part of an active noise cancellation system, whether it be a feedforward, feedback or hybrid system.

The headphone 100 may also operate in a passthrough or transparency mode in which sound incident at the microphone 106, positioned on an external surface of the headphone, is applied to the one or more loudspeakers 102 so that a user wearing the headset 100 is able to hear their ambient acoustic environment which has otherwise been occluded due to them wearing the headset 100 and therefore has ambient awareness.

In the embodiments described herein, where feedback and/or feedforward ANC or passthrough is implemented, the microphones 104, 106 may be used both for performing feedback and/or feedforward ANC or passthrough and for providing the heartbeat noise cancellation as is described in detail below. In other embodiments, separate microphones may be provided for performing one or more of these functions. For example, the headphone 100 may comprise the internal microphone 104 for use in cancellation or reduction of audible heartbeat and an additional microphone (not shown) may be used for one or more additional ANC functions.

In the example shown in FIG. 1, an intra-concha headphone 100 is provided as an example personal audio device. It will be appreciated, however, that embodiments of the present disclosure can be implemented on any personal audio device which is configured to be placed at, in or near the ear of a user. Examples include circum-aural headphones worn over the ear, supra-aural headphones worn on the ear, in-ear headphones inserted partially or totally into the ear canal to form a tight seal with the ear canal, or mobile handsets held close to the user's ear so as to provide audio playback (e.g. during a call). Embodiments of the present disclosure may be implemented in any type of headset that comprises at least one headphone operable to partially or fully occlude the ear. Examples include virtual reality headsets, augmented reality headsets and smart glasses to name a few.

Figure 2:
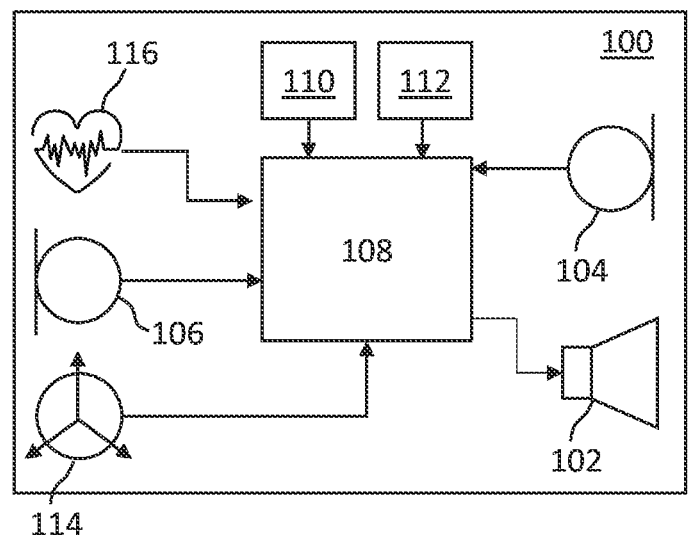
FIG. 2 is a schematic diagram of the headphone of FIG. 1.

FIG. 2 is a system schematic of the headphone 100. The headphone 100 may form part of a headset comprising another headphone (not shown) configured in substantially the same manner as the headphone 100. The pair of headphones (the headphone 100 and the other headphone which is not shown) may form a stereo headset.

A signal processor 108 of the headphone 100 is configured to receive microphone signals from the microphones 104, 106 and output audio signals to the loudspeaker 102. When the headphone 100 is positioned at, near or within the ear canal, the microphone 104 is occluded to some extent from the external ambient acoustic environment. The headphone 100 may be configured for a user to listen to music or audio, to make telephone calls, to deliver voice commands to a voice recognition system, and/or other such audio processing functions. The processor 108 may be configured to implement active noise cancellation (feedback and/or feedforward) and/or passthrough/transparency modes using the microphones 104, 106 and the one or more transducers 102.

The headphone 100 further comprises a memory 110, which may in practice be provided as a single component or as multiple components. The memory 110 is provided for storing data and/or program instructions. The headphone 100 further may further comprise a transceiver 112, which is provided for allowing the headphone 100 to communicate (wired or wirelessly) with external devices, such as another headphone, and/or a host device, such as a mobile device (e.g. smartphone) for example, to which the headphone 100 is coupled. Such communications between the headphone 100 and external device(s) may comprise wired communications where suitable wires are provided between left and right sides of a headset, either directly such as within an overhead band, or via an intermediate device such as a mobile device and/or wireless communications. The headphone may be powered by a battery and may comprise other sensors (not shown).

The headphone 100 may further comprise an inertial measurement unit (IMU) 114 sensor, such as an accelerometer or gyroscope, which may be configured to output inertial measurements to the processor 108. The IMU 114 may form part of the headphone 100. Alternatively, the IMU 114 may be a separate module in communication with the headphone 100, for example, via the transceiver 112.

The headphone 100 may further comprise a heartbeat (HB) monitor 116, for example an optical HB monitor, configured to measure one or more characteristics of the heartbeat of the user wearing the headphone 100. The HB monitor 116 may form part of the headphone 100. Alternatively, the HB monitor 116 may be a separate module in communication with the headphone 100, for example via the transceiver 112. For example, the HB monitor 116 may be integrated into a strap or watch worn by the user. The HB monitor may be configured to measure characteristics of a heartbeat optically and/or electrically, for example using photoplethysmography (PPG), electroencephalography (EEG), electrocardiography (ECG) or any other method used in the art.

Heartbeat characteristics may include but are not limited to heart or pulse rate (i.e. the number of cycles of contraction and dilation of the heart over a predetermined period of time) and heart rhythm (e.g. the temporal pattern in which muscles of the heart contract and dilate and the temporal pattern in which the valves of the heart open and close). It will be understood that with each of these events in the heart there is associated a sound which may be audible to the user.

As mentioned above, when a user is wearing the headphone 100, particularly in the form shown in FIG. 1 that occludes the user's ear canal, the pulsing of blood through blood vessels close to their ear drum causes a heartbeat noise to be present in the user's hearing, such heartbeat noise being more pronounced in a fully occluded ear canal. Embodiments of the present disclosure aim to reduce or cancel heartbeat noise audible to the user by applying an anti-heartbeat noise to the user's ear, via the transducer 102 of the headphone 100 which is generated in dependence on a measured signal representative of the user's heartbeat. The anti-heartbeat noise may be tailored specifically to the characteristic of the user's own heartbeat, such as the user's heartrate or heart rhythm.

As will be described in more detail below, the signal representative of the user's heartbeat may be derived in several ways using one or more of the internal and/or external sensors such as the microphone 104, the IMU 114 and/or the heartbeat sensor 116. The heartbeat noise cancellation signal, i.e. the anti-heartbeat noise, may also be derived in several ways as will also be described below.

Figure 3:
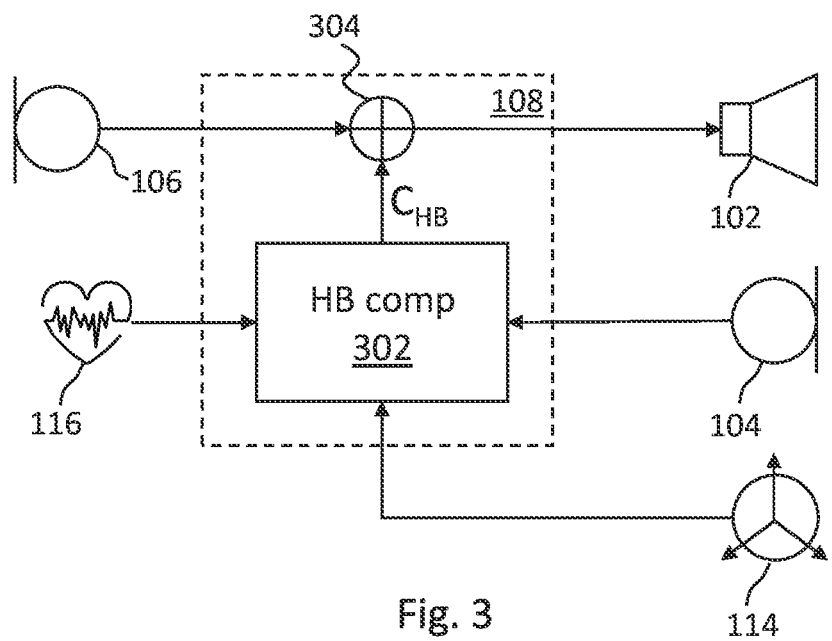
FIG. 3 is a schematic diagram illustrating a processor of the headphone of FIGS. 1 and 2 in more detail.

FIG. 3 is a block diagram showing the signal processor 108 according to some embodiments of the disclosure. For clarity, the memory 110 and transceiver 114 are not shown. The processor 108 comprises a heartbeat compensation module 302 configured to generate a heartbeat noise cancelation signal $C_{HB}$ which may be output to the speaker 102 for cancellation of heartbeat noise in the user's hearing. The processor 108 is shown in FIG. 3 in a passthrough mode in which signals received at the external microphone 106 of the headset are provided to the transducer 102 such that the user of the headphone 100 is able to hear ambient noise (as is described in more detail above). Embodiments of the disclosure may be particularly applicable to headsets implementing passthrough. When passthrough is enabled in a headset, it is likely that the user is trying to experience their acoustic ambient environment. In such circumstances, with only the ambient sound at the external microphone 106 being output to the transducer 102, the heartbeat of the user may be more audible to the user when compared to other headset modes, such as when media is being played back through the transducer 102. To implement passthrough, the processor 108 may comprise a summing module 304 configured to combine the signal being passed through to the speaker 102 and the heartbeat compensation signal $C_{HB}$. In other embodiments, the passthrough functionality shown in FIG. 3 and described herein may be omitted.

It will be appreciated that further variations of the headphone 100 may implement feedforward and/or feedback ANC in combination with heartbeat compensation, examples of which will be described in more detail below.

The heartbeat compensation module 302 may be configured to receive one or more heartbeat signals from one or more internal and/or external sensors. For example, the heartbeat compensation module 302 may receive an audio signal from the internal or error microphone 104 which may pick up the sound of the user's heartbeat in the ear canal. A phonocardiogram (PCG) may therefore be extracted from the audio signal received at the internal microphone 104. Additionally, or alternatively, the heartbeat compensation module 302 may receive an IMU signal from the IMU 114. When the IMU 114 is positioned in the headphone 100, vibrations associated with the user's heartbeat, such as movement of blood through blood vessels, may travel through the user's head and transfer to the headphone 100 to then be picked up by the IMU 114. Similar transfer of vibrations associated with the heartbeat sensed by the IMU 114 may also occur if the IMU 114 is mechanically coupled (directly or indirectly) with the user's body, such as in the nose-bridge of a pair of smart classes for example. Additionally, or alternatively, the heartbeat compensation module 302 may receive a heartbeat signal from the heartbeat sensor 116. As mentioned above, the heartbeat sensor 116 may be configured to measure a heartbeat optically or electrically, for example using photoplethysmography (PPG), electroencephalography (EEG), electrocardiography (ECG) or any other method used in the art for heartbeat monitoring. As mentioned above, the heartbeat sensor 116 may be integrated into the headphone 100 or may be separate from the headphone 100.

Figure 4:
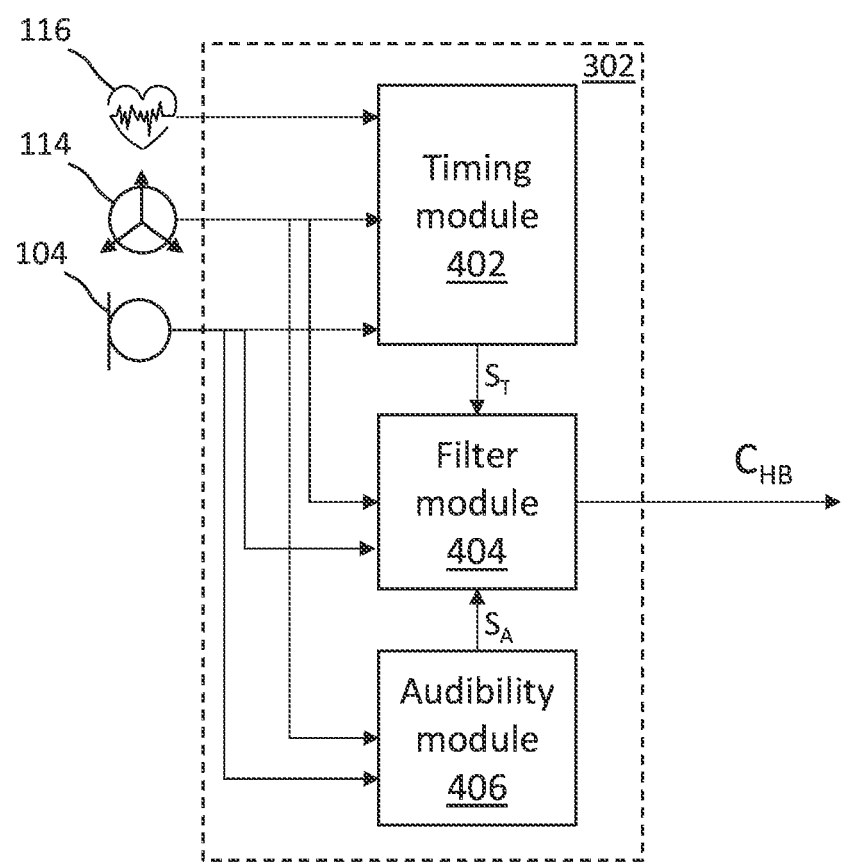
FIG. 4 is a schematic diagram of a heartbeat compensation module according to embodiments of the disclosure.

FIG. 4 shows the heartbeat compensation module 302 in more detail. The heartbeat compensation module 302 may comprise a timing module 402, a filter module 404 and a audibility module 406.

The timing module 402 may be configured to extract timing information associated with the heartbeat of the user from one or more of the signals received from the sensors, i.e. the internal or error microphone 104, the IMU signal received from the IMU 114 and the heartbeat signal received from the heartbeat sensor 116. Timing information may include a heartrate of the user as well as features of heart rhythm, e.g. timing of muscle and valve events in the heart. Such features may coincide with audio artefacts heard by the user due to the heartbeat.

Figure 5:
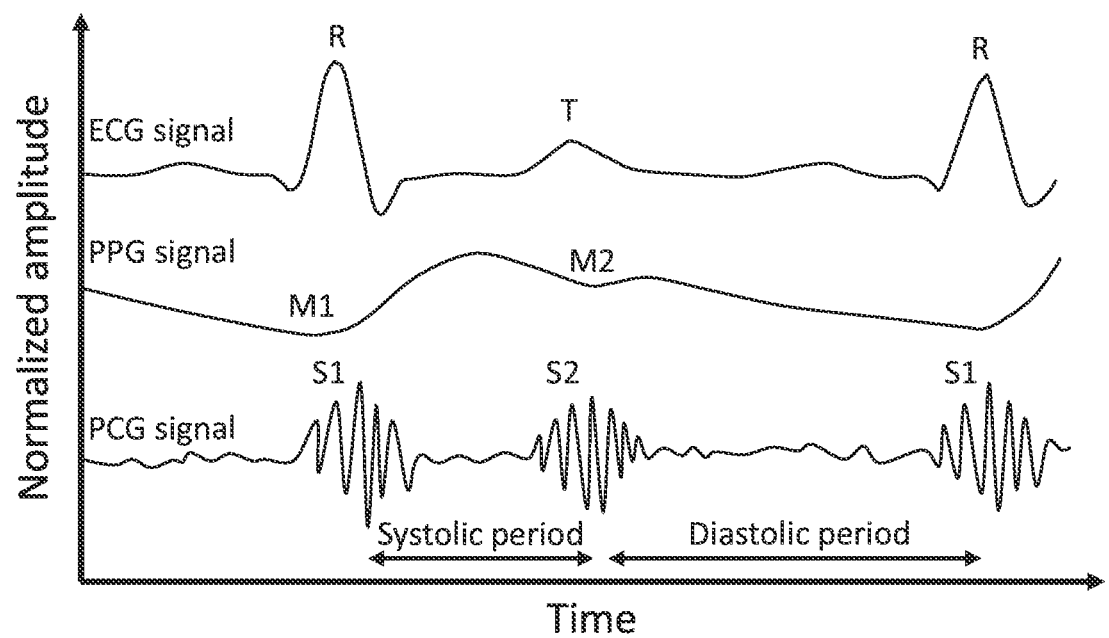
FIG. 5 is a graph showing various waveforms of a human heartbeat generated using electrocardiography (ECG), photoplethysmography (PPG) and phonocardiography (PCG)

FIG. 5 is an illustration of three physiological signals (ECG, PPG and PCG) monitoring a typical heartbeat which may be used to obtain heartbeat timing information. The PCG (which may be extracted from the audio signal received from the internal or error microphone 104) comprises two features, known in the medical field as S1 and S2, which may be associated with noise in the user's ear. The S1 sound represents the closure of the atrioventricular (mitral and tricuspid) valves of the heart as the ventricular pressures exceed atrial pressures at the beginning of systole. The S2 sound represents closure of the semilunar (aortic and pulmonary) valves.

The corresponding PPG signal comprises a first minima which coincides with the onset of the S1 sound in the PCG and a second minima which coincides with the S2 sound in the PCG. The corresponding ECG signal comprises a large spike (known as the R wave) which coincides with the onset of the S1 sound in the PCG and a second smaller spike (known as the T wave) that coincides with the onset of the S2 sound in the PCG. Thus, by processing signals output from one or more of the internal or error microphone 104, the IMU unit 114 and the heartbeat sensor 116 timing information related to the heartbeat of the user can be ascertained. It will be appreciated from FIG. 5, that the human heartbeat comprises several components which each may have different audio characteristics. As such, as will be described in more detail below, it may be preferable to control any noise cancellation signal based on which component of the heartbeat is audible to the user so as to tailor, whether automatically or manually, the noise cancellation to the sound of the components of the heartbeat.

Referring again to FIG. 4, the audibility module 406 may be configured to monitor a sound level at the headset 100 and determine whether the sound level is such that the user may be able to hear their heartbeat. The audibility module 406 may receive signals from one or more of the internal error microphone 104, and the IMU 114. Although not shown in FIG. 4, the audibility module 406 may additionally or alternatively receive a microphone signal from the external microphone 106. Additionally or alternatively, the audibility module 406 may receive other signals, such as a signal from the user themselves indicating that they can hear their own heartbeat in their ear. The audibility module 406 may output an audibility signal $S_A$ indicating whether the user can (or whether it is likely that the user can) hear their heartbeat in their ear.

Figure 6:
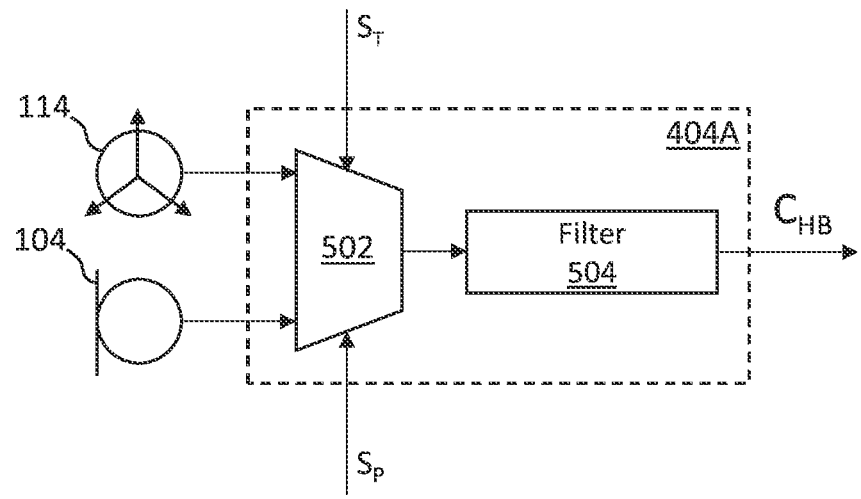
FIG. 6 is a schematic diagram of a filter module according to embodiments of the disclosure.
Figure 7:
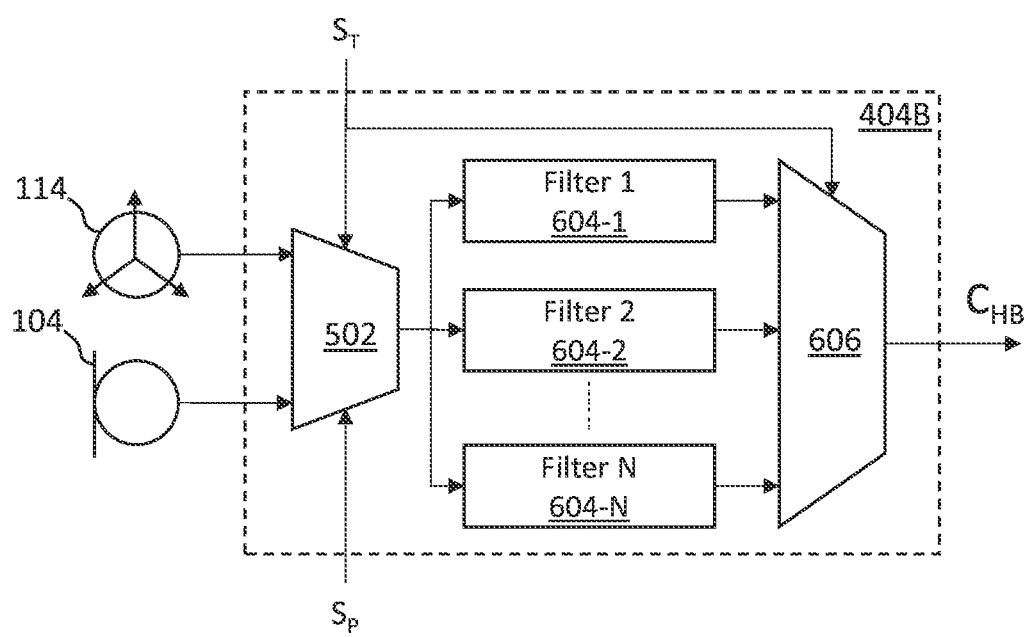
FIG. 7 is a schematic diagram of a filter module according to embodiments of the disclosure.

The filter module 404 is configured to receive timing information from the timing module 402 and generate the heartbeat compensation signal $C_{HB}$ (or heartbeat noise cancellation signal) by filtering one of the audio signal received from the internal error microphone 104 and the IMU signal received from the IMU 114. FIGS. 6 and 7 provide two example implementations 404A, 404B of the filter module 404, denoted in these figures as 404A and 404B respectively. Like parts of the two implementations 404A, 404B have been given like numbering.

FIG. 6 illustrates the first exemplary implementation 404A of the filter module 404 according to some embodiments of the disclosure. The filter module 404A comprises a selector module 502 and a compensation filter 504. The selector module 502 is configured to select between using the error microphone 104 signal and the IMU signal as the basis of the heartbeat compensation signal $C_{HB}$. It will be appreciated that where only one of the error microphone 104 and the IMU 114 provides a signal to the filter module 404A, the functionality may not be present.

The selector module 502 may be further configured to select that neither of the received audio and IMU signals are passed to the compensation filter 504. In other words, the selector module 502 may gate the output of the heartbeat compensation signal $C_{HB}$. This selection or gating may be based on the received timing information signal $S_T$ and the audibility signal $S_P$. For example, the selector module 502 may control the filter module 404A and may be configured to output a heartbeat compensation signal $C_{HB}$ only when a heartbeat is present (or is likely to be present) in the hearing of the user, based on the received audibility signal $S_P$. For example, the selector module 502 may select between the audio signal and the IMU signal based on the timing information signal $S_T$ which in turn may be based on timing information and/or signal quality information about the signals received from each of the internal microphone 104 and the IMU 114.

The selector module 502 may then pass one of the signals from the internal microphone 104 or the IMU 114 to the compensation filter 504 which filters the selected signal and outputs the filtered selected signal as the heartbeat compensation signal (or heartbeat noise cancellation signal) $C_{HB}$. In some embodiments, the selector module 502 may be configured to pass both of the signals from the internal microphone 104 and the IMU 114 to the compensation filter 504.

FIG. 7 illustrates another implementation 404B of the filter module 404. As with the implementation 404A shown in FIG. 6, the filter module 404B comprises a selector module 502 configured to select between using the audio signal and the IMU signal as the basis of the heartbeat compensation signal $C_{HB}$ or deselecting both input signals, based on the timing signal $S_T$ and the audibility signal $S_P$. In some embodiments, the selector module 502 may be configured to select both input signals. Operation of the selector module 502 is described above. In contrast to the filter module 404A, the filter module 404B comprises a filter bank 604 comprising a plurality of compensation filters 604-1:604-N. Three compensation filters are shown, but two or more than three compensation filters may be provided. The selected signal from the selector module 502 is provided to each of the plurality of filters 604-1:604-N of the filter bank 604. Each compensation filter 604 is configured to filter selected signal and output a filtered version of the selected signal to a multiplexer 606 controlled in dependence on the timing signal $S_T$. The multiplexer 606 may be configured to output one of the filtered signal received from the filter bank 604. In a variation of the above, the selector module 502 may be configured to pass each of the input signals to a different one or more of the compensation filters 604-1:604-N.

As mentioned above with reference to FIG. 5, the human heartbeat comprises several components which each may have different audio characteristics. By providing multiple filters, the different heartbeat components audible to the user may be cancelled using different noise cancellation signals. Thus, the multiplexer 606 may switch between the filtered signals output from each of the compensation filters 604-1:604-N in dependence on the timing of the heartbeat to generate a heartbeat compensation signal that most effectively cancels the heartbeat noise audible to the user.

In a variation of the embodiment shown in FIG. 7, the filter bank 604 may be replaced with a single filter, the coefficients of which may be adapted over time based on the received timing signal $S_T$ so as to achieve the same effect as switching between multiple discrete filters.

Figure 8:
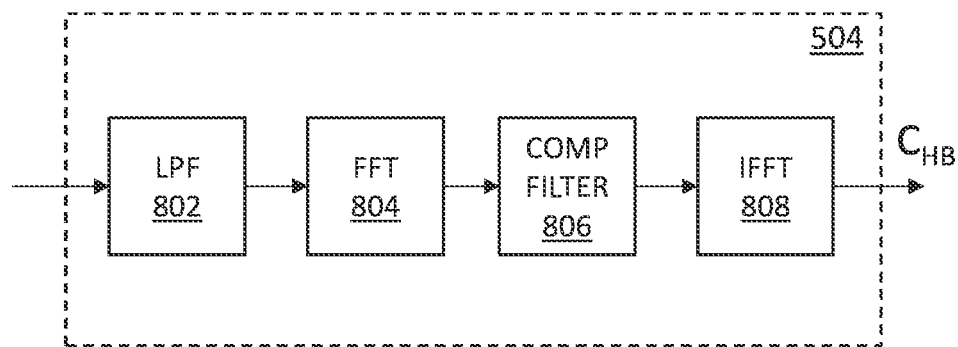
FIG. 8 is a schematic diagram of a filter of the filter module shown in FIG. 6.

FIG. 8 is a schematic diagram illustrating an example implementation of the filter 504 shown in FIG. 6. The filters 604-1:604-N of the filter bank 604 shown in FIG. 7 may be implemented similarly.

The filter 504 may comprise a low pass filter 802, a fast Fourier transform (FFT) module 804, compensation filter stage 806, and an inverse fast Fourier transform (IFFT) module 808.

The low pass filter 802 may be configured to remove noise associated with non-heartbeat sound, such as sound due to playback through the transducer 102. For example, the low pass filter 802 may have a cut-off frequency of 300 Hz, or 250 Hz.

The low pass filtered signal filtered by the low pass filter 802 may then be provided to a fast Fourier transform (FFT) module 804 operable to convert the received signal into the digital domain by applying a Fourier transform, such as an FFT to the low pass filtered signal. The FFT module 804 may transform the signal over a predetermined range which may be chosen to span the possible range of heartrate of the user. For example the FFT may be over the range of 20 Hz to 240 Hz.

The digital signal output from the FFT module 804 may then be provided to compensation filter stage 806 which may comprise a plurality of filter taps each operable to filter a respective frequency component of the digital signal output from the FFT module 804. For example, the compensation stage 806 may comprise taps spanning the frequency range associated with the human heartbeat. For example, the compensation stage may have 4 or more taps, more preferably 6 or more taps. More filter taps may be provided at common heartrates, for example in the range of 50 Hz to 180 Hz. For example, the compensation filter stage 806 may have filter taps centred at frequencies of 10 Hz, 20 Hz, 40 Hz, 80 Hz, 160 Hz and 240 Hz.

A compensated signal may then be output from the compensation stage 806 in the digital domain and provided to the IFFT module 808 for conversion back into the analogue domain and output from the IFFT module 808 as the heartbeat compensation signal $C_{HB}$.

Figure 9:
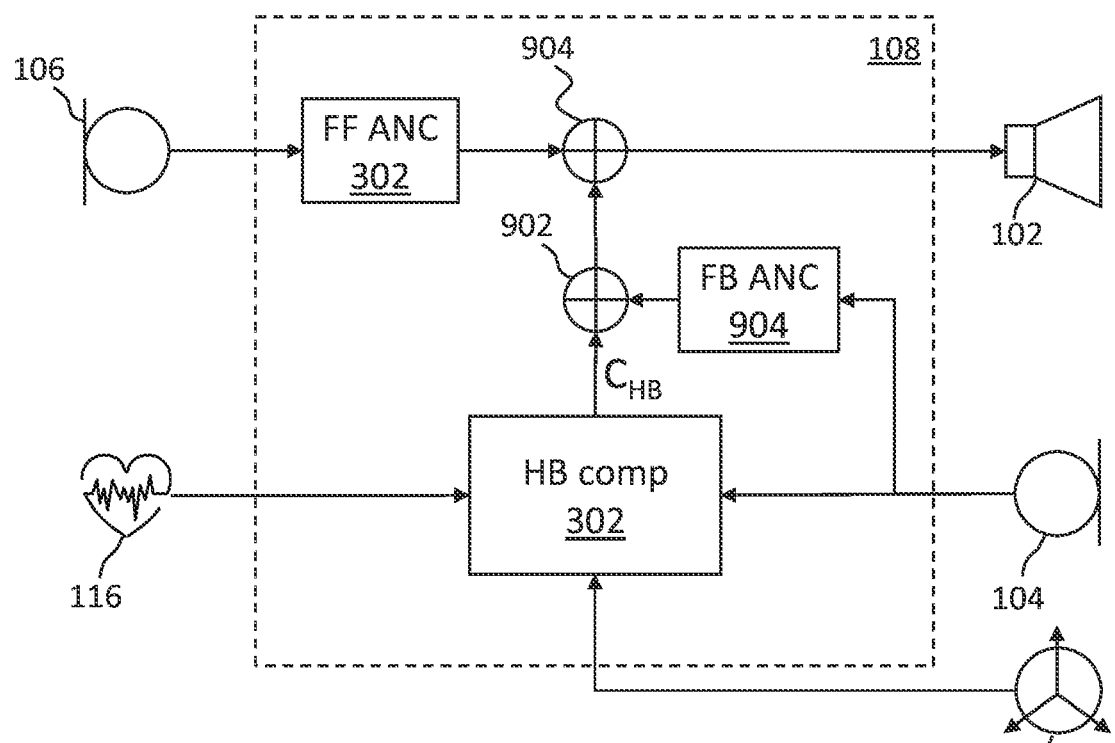
FIG. 9 is a schematic diagram of a variation of the processor shown in FIG. 3.

FIG. 9 is a variation of the implementation of the processor 108 shown in FIG. 3 comprising an ANC solution in which heartbeat compensation is combined with conventional feedforward and/or feedback ANC, where like parts have been provided with like numberings.

The heartbeat compensation signal $C_{HB}$ may be provided to a first summing module 902 configured to combine the output of a feedback ANC module 804. The feedback ANC module 904 may operate conventionally and so will not be described in more detail here. The first summing module 902 may be configured to selectively combine the feedback ANC signal and the heartbeat compensation signal depending on whether feedback ANC and/or heartbeat compensation is switched off. It will be appreciated that abrupt switching in and out of the heartbeat compensation signal $C_{HB}$ and the feedback ANC signal may lead to artefacts in the signal provided to the transducer. Accordingly, in some embodiments, the processor 108 may be configured to apply smoothing in a manner known in the art during transition/selection.

The combined signal combined by the summing module 902 may be provided to a second summing module 904 which may combine that signal with a feedforward ANC signal received from a feedforward ANC module 908 configured to generate a feedforward ANC signal based on the external (e.g. reference) microphone signal from the external microphone 106. The feedforward ANC module 908 may operate conventionally and so will not be described in more detail here. Again, the second summing module 904 may be configured to selectively combine signals depending on whether feedforward ANC and/or passthrough is required.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog TM or VHDL (Very high-speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. Circuitry for noise cancellation in a headset worn by a user, the circuitry comprising:
an input for receiving one or more heartbeat signals representative of a heartbeat of the user;
a processor for generating a heartbeat noise cancellation signal based on the one or more heartbeat signal, the heartbeat noise cancellation signal to cancel a noise associated with the heartbeat in the user's ear;
an output for outputting the heartbeat noise cancellation signal to a transducer of the headset, wherein the one or more heartbeat signals is received from a photoplethysmography (PPG) sensor or an electrocardiography (EGC) sensor.

2. Circuitry of claim 1, wherein the one or more heartbeat signals comprises one or more of:
a) an audio signal from an internal microphone of the headset;
b) an IMU signal from an inertial measurement unit, IMU of the headset.

3. Circuitry of claim 2, wherein the processor is configured to:
filter the audio signal or the IMU signal; and
output the filtered audio signal or the filtered IMU signal as the heartbeat noise cancellation signal.

4. Circuitry of claim 3, wherein filtering of the audio signal or the IMU signal comprises:
applying a low pass filter to remove noise.

5. Circuitry of claim 3, wherein filtering of the audio signal or the IMU signal comprises:
adjusting a gain of one or more frequency components of the audio signal or the IMU signal at frequencies of the noise associated with the heartbeat in the user's ear.

6. Circuitry of claim 3, wherein the processor is configured to monitor timing of the heartbeat based on the one or more heartbeat signals and filter the audio signal or the IMU signal based on the timing.

7. Circuitry of claim 6, wherein the timing of the heartbeat comprises a heartrate.

8. Circuitry of claim 6, wherein the timing of the heartbeat comprises a heart rhythm.

9. Circuitry of claim 8, wherein the heart rhythm comprises one or more of:
a) timing of a contraction or dilation of one or more muscles of the heart; and
b) timing of an opening or closing of one or more valves of the heart.

10. Circuitry of claim 6, wherein the processor is configured to filter the audio signal with a first filter characteristic during a first time period and a second filter characteristic during a second time period.

11. Circuitry of claim 10, wherein the first time period is an S1 period of a cardiac cycle and the second time period is an S2 period of a cardiac cycle.

12. Circuitry of claim 10, wherein the processor is configured to switch between a first filter for applying the first filter characteristic and a second filter for applying the second filter characteristic to the audio signal.

13. Circuitry of claim 10, wherein the processor is configured to change a one or more filter co-efficients of a common filter to switch between filtering the audio signal with the first filter characteristic and filtering the audio signal with the second filtering characteristic.

14. Circuitry of claim 3, wherein the one or more characteristics of the filtering is dependent on an amplitude of one or more features in one or more of the one or more heartbeat signals.

15. Circuitry of claim 2, wherein the processor is configured to:
monitor a sound level at the headset; and
generate the heartbeat noise cancellation signal when the sound level is below a predetermined threshold level at which the noise associated with the heartbeat is audible to the user.

16. Circuitry of claim 15, wherein the sound level is monitored using one or more of the IMU signal, or the audio signal from the internal microphone, or an audio signal from an external microphone of the headset.

17. Circuitry of claim 2, wherein the processor is further configured to generate a feedback noise cancellation signal based on the audio signal received from the internal microphone; and
wherein the output is configured to output the feedback noise cancellation signal to the transducer.

18. Circuitry of claim 1, wherein the processor is configured to:
generate the heartbeat noise cancellation signal when a heartrate of the heartbeat exceeds a predetermined heartbeat threshold at which the noise associated with the heartbeat is audible to the user.

19. Circuitry of claim 1, further comprising a second input for receiving an external audio signal from an external microphone;
wherein the processor is further configured to generate a feedforward noise cancellation signal based on the external audio signal from the external microphone;
wherein the output is configured to output the feedforward noise cancellation signal to the transducer.

20. A headphone comprising the circuitry of claim 1.

21. The headphone of claim 20, wherein the headphone may be configured to partially or fully occlude the ear of the user.

22. An electronic device comprising circuitry as claimed in claim 1, wherein the electronic device is at least one of: a portable device; a battery powered device; a communications device; a computing device; a mobile telephone; a laptop, notebook or tablet computer; a personal media player; a gaming device; and a wearable device.

23. A headphone, comprising:
an internal microphone;
an external microphone;
a transducer; and
one or more processors configured to:
receive one or more heartbeat signals representative of a heartbeat of a user;
generate a heartbeat noise cancellation signal based on the one or more heartbeat signal, the heartbeat noise cancellation signal to cancel a noise associated with the heartbeat in the user's ear; and
output the heartbeat noise cancellation signal to the transducer, wherein the one or more heartbeat signals is received from a photoplethysmography (PPG) sensor or an electrocardiography (ECG) sensor.

24. Circuitry configured to:
obtain a heartbeat signal for a user from a photoplethysmography (PPG) sensor or an electrocardiography (ECG) sensor;
apply an anti-noise signal to the ear of the user to cancel a sound of the user's heartbeat in the user's ear, based on the heartbeat signal.

25. A headphone, comprising:
a speaker; and
a signal processor configured to:
receive one or more signals representative of a heartbeat of a user from a photoplethysmography (PPG) sensor or an electrocardiography (ECG) sensor;

generate a heartbeat noise cancellation signal based on the one or more representative signals and output the heartbeat noise cancellation signal to the speaker.

26. Circuitry configured to:
receive a heartbeat signal from a photoplethysmography (PPG) sensor or an electrocardiography (ECG) sensor;
generate, based on the heartbeat signal, an anti-heartbeat for application to a speaker.

27. Circuitry configured to:
receive a signal representative of the function of a human heart from a photoplethysmography (PPG) sensor or an electrocardiography (ECG) sensor;
generate, based on the heartbeat signal, an anti-phase signal representative of the function of a human heart for application to a speaker.

28. Circuitry for noise cancellation in a headset worn by a user, the circuitry comprising:
an input for receiving one or more heartbeat signals representative of a heartbeat of the user;
a processor for generating a heartbeat noise cancellation signal based on the one or more heartbeat signals when a heartrate of the heartbeat exceeds a predetermined heartbeat threshold at which a noise associated with the heartbeat is audible to the user, the heartbeat noise cancellation signal to cancel a noise associated with the heartbeat in the user's ear;
an output for outputting the heartbeat noise cancellation signal to a transducer of the headset.

29. Circuitry for noise cancellation in a headset worn by a user, the circuitry comprising:
an input for receiving one or more heartbeat signals representative of a heartbeat of the user;
a processor for generating a heartbeat noise cancellation signal based on the one or more heartbeat signal, the heartbeat noise cancellation signal to cancel a noise associated with the heartbeat in the user's ear;
an output for outputting the heartbeat noise cancellation signal to a transducer of the headset,
wherein the one or more heartbeat signals comprises one or more of an audio signal from an internal microphone of the headset or an IMU signal from an inertial measurement unit (IMU) of the headset,
wherein the processor is configured to:
monitor timing of the heartbeat based on the one or more heartbeat signals;
filter the audio signal or the IMU signal based on the timing, the filtered audio signal output as the heartbeat noise cancellation signal.

\* \* \* \* \*